US00PP28920P3

(12) United States Plant Patent
Solberg

(10) Patent No.: US PP28,920 P3
(45) Date of Patent: Jan. 30, 2018

(54) ***HOSTA* PLANT NAMED 'FIRST BLUSH'**

(50) Latin Name: ***Hosta* hybrid**
Varietal Denomination: First Blush

(71) Applicant: Robert M. Solberg, Franklinton, NC (US)

(72) Inventor: Robert M. Solberg, Franklinton, NC (US)

( * ) Notice: Subject to any disclaimer, the term of this patent is extended or adjusted under 35 U.S.C. 154(b) by 15 days.

(21) Appl. No.: 14/998,503

(22) Filed: Jan. 14, 2016

(65) Prior Publication Data

US 2017/0208726 P1 Jul. 20, 2017

(51) Int. Cl.
*A01H 5/12* (2006.01)

(52) U.S. Cl.
USPC ..... Plt./353

(58) Field of Classification Search
USPC ..... Plt./353

CPC ..... A01H 5/0272; A01H 5/02; A01H 5/12; A01H 5/00
See application file for complete search history.

(56) References Cited

PUBLICATIONS

*Hosta* Choice Gardens Internet Availability 2016 retrieved on Apr. 18, 2017, retrieved from the Internet at <https://www.hostachoicegardens.com/images/2016_Internet_Availability_10.pdf> pp. 1 and 17.*

* cited by examiner

*Primary Examiner* — June Hwu

(57) ABSTRACT

A new and distinct cultivar of *Hosta* named 'First Blush', characterized by its medium sized mounding clump, green leaves with purplish-red colored petioles on both sides, that emerge with a thin purplish-red margin, become ("blush") purplish-red on the upward side of the leaf blade in the space between the veins, and producing dark purple pink flowers on purplish-red scapes. In combination these traits set 'First Blush' apart from all other existing varieties of *Hosta* known to the inventor.

3 Drawing Sheets

Latin name: *Hosta* hybrid.
Variety denomination: 'First Blush'.

BACKGROUND OF THE INVENTION

The present invention relates to a new and distinct cultivar of *hosta* plant, botanically known as *Hosta*, hereinafter referred to by the cultivar name 'First Blush'.

The new plant was hybridized and developed by the Inventor in Chapel Hill, N.C., USA as a result of a hybrid cross between the pod parent *Hosta* 'Beet Salad' (not patented) and the pollen parent, an unnamed *Hosta* seedling of the Inventor (not patented). The new plant differs from its female parent primarily in that areas of the leaves produce anthocyanins that produce a purplish-red "blush" on the upper surface of the leaf. The pollen parent is no longer available for observation. Asexual propagation of the new cultivar by division in 2011 in Franklinton, N.C. USA and by meristem tissue culture in 2014 in Rochelle, Ill. USA has shown the unique and distinct characteristics of this new plant are stable and reproduce true to type in successive generations.

SUMMARY OF THE INVENTION

The following traits have been repeatedly observed and are determined to be the unique characteristics of 'First Blush'. These characteristics in combination distinguish the new *hosta* as a new and unique cultivar:

1. Medium sized mounding clump;
2. Green leaf with purplish-red colored petioles on both sides;
3. Green leaf that emerges with a thin purplish-red margin;
4. Green leaf that becomes ("blushes") purplish-red on the upward side of the leaf blade in the space between the veins;
5. Dark purple pink flowers on purplish-red scapes.

The new *hosta* can be compared to the cultivar, *Hosta* 'Purple Haze' (not patented). In the new *hosta*, the leaf margin has a thin red margin as compared to the margin of *Hosta* 'Purple Haze' which has no red margin. The leaf of the new *hosta* becomes purplish-red on the upper service of the leaf between the veins and persists for several weeks compared to the leaf of *Hosta* 'Purple Haze' that has a purple color in parts of the leaf that persists a shorter period of time. The leaf of the new *hosta* does not have glaucous wax on its leaves giving its leaves a green color compared to the leaves of *Hosta* 'Purple Haze' that have glaucous wax giving the leaf a bluish color.

The new *hosta* cultivar has not been observed under all possible environmental conditions. The phenotype may vary to some extent with variations in environmental conditions such as temperature, fertility and light intensity, but without any variance in the genotype.

BRIEF DESCRIPTION OF THE PHOTOGRAPHS

The accompanying color photographs illustrate the overall appearance of the new cultivar including its unique traits as a 4 year old plant growing in a one quart container. The colors are as true as is reasonably possible with conventional photography.

Figure 1:
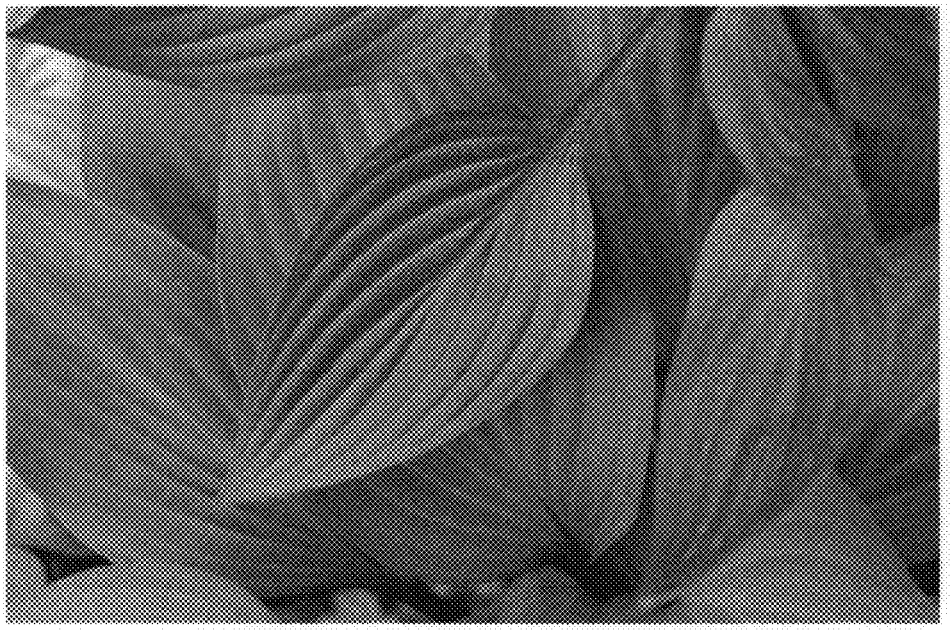

FIG. 1 was taken in May and comprises a top perspective of an individual leaf of the new *hosta* compared to its green leafed sibling seedling.

Figure 2:
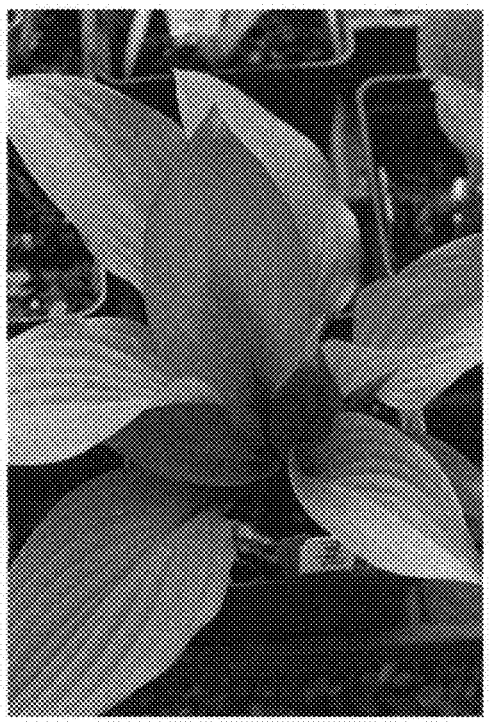

FIG. 2 was taken in April and shows the entire *hosta* clump with thin purplish-red margin.

Figure 3:
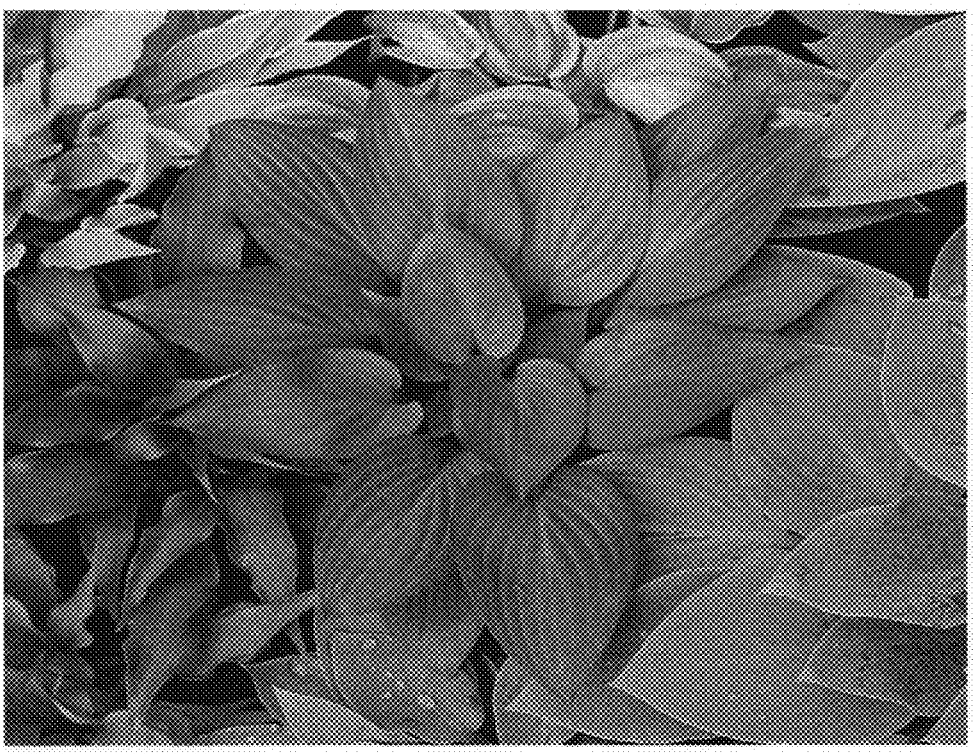

FIG. 3 was taken in May and shows the entire *hosta* clump centered among other *hosta* varieties.

Figure 4:
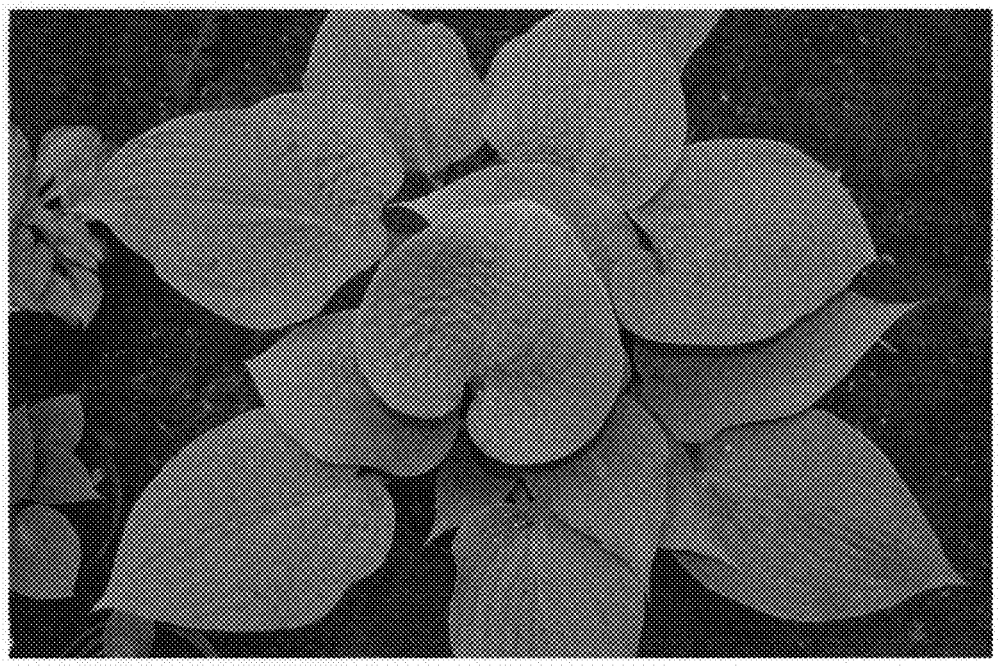

FIG. 4 shows entire clump of 'Purple Haze' for comparison.

Figure 5:
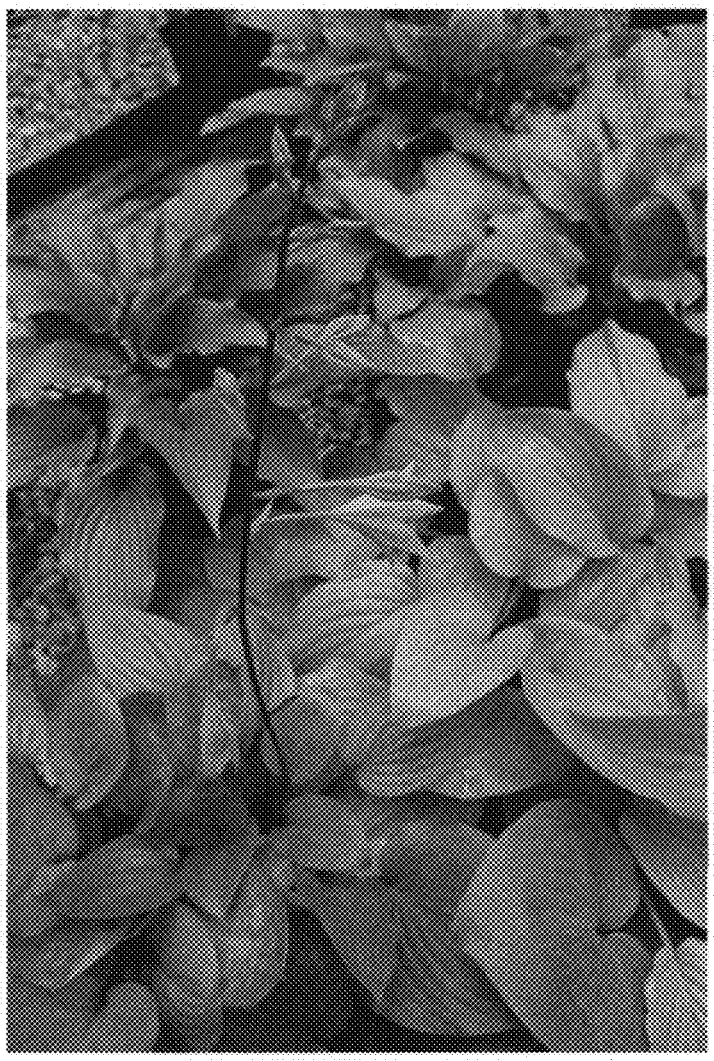

FIG. 5 was taken in July and shows the new *hosta* flower scape.

DETAILED DESCRIPTION OF THE INVENTION

In the following description, color references are made to The Royal Horticultural Society's Colour Chart (2001 edition) except where general terms of ordinary dictionary significance are used. The following observations and measurements describe a 4-year old plant growing in a one quart container, as depicted in the accompanying photographs, which was grown outdoors in Franklinton, N.C., USA.

Botanical classification: *Hosta* 'First Blush'.

Parentage: *Hosta* 'Beet Salad' (not patented) times unnamed *Hosta* seedling of the Inventor.

Propagation:

*Method*.—By division and meristem tissue culture.

Plant description:

*Plant habit*.—Compact, mounding, symmetrical.

*Culture*.—Light to medium shade in moist, well-drained soil.

*Plant type*.—Herbaceous rhizomatous perennial.

*Plant height*.—14 inches.

*Plant width*.—28 inches.

*Growth rate*.—Vigorous.

*Root system*.—Normal, fleshy, branching from central rhizome.

*Disease resistance*.—No known resistance or susceptibility to disease known to *Hosta* has been observed.

*Plant hardiness zone*.—3-9.

Foliage description:

*Leaf shape*.—Ovate with a rounded base and acute tip.

*Leaf margin*.—Entire.

*Leaf surface*.—Smooth, slightly shiny.

*Leaf texture*.—Moderate substance, veins impressed, leaf blade twisting absent.

*Leaf dimensions*.—5 inches in width, 8½ inches in length.

*Venation pattern*.—Campylodrome with 6 to 7 pairs of veins, the same color as the leaves brilliant yellowish green (about RHS 149A) except on the upper and lower surfaces at the base of the leaf where they are the color of the petiole moderate red (RHS 179A).

*Leaf color*.—The leaves in spring are brilliant yellowish green (about RHS 149A) with a thin, about ⅛ inches, moderate reddish orange margin (about RHS 178C). The back of the leaves are light yellowish green (about RHS 142C). The areas of the leaves between the veins produce anthocyanins that produce a ("blush") purplish-red (about RHS 178B) on the upper surface of the leaf after the second set of leaves begin to appear. The leaves become strong yellow green (about RHS 144C) later in the season during the blooming period on both sides of the leaf.

Petiole description: Plant petioles have a length of approximately 7 to 8 inches with a diameter of about ½ to ⅝ inches and U-shaped. The petiole color is moderate red (RHS 179A) and extends up into the leaf midrib ⅓ to ½ toward the leaf tip.

Flower description:

*Bloom period*.—Mid-summer (mid-July-August in Franklinton, N.C.).

*Fragrance*.—None.

*Flower arrangement*.—Raceme of numerous single horizontal to drooping flowers comprised of six tepals. The number of flowers per raceme varies from about 15 to 20 with each flower lasting approximately one day over a period of about 3 weeks.

*Flower shape*.—Funnel-shaped.

*Flower dimensions*.—3 inches in length and 2 inches in width.

*Flower color*.—Dark purple pink (about RHS 186C).

*Bud color*.—Dark purple pink (about RHS 186C).

*Bud dimensions*.—2¼ inches in length and ½ inches in width.

*Tepal color*.—Inner moderate purple pink (about RHS 186B); outer dark purple pink (about RHS 186C); inner border ⅛ to 3/16 inches wide, yellowish white (about RHS 155B); outer base (tube) lower ⅞ inches, moderate purplish red (about RHS 184D).

*Tepal apex shape*.—Acute.

*Tepal dimensions*.—2 inches in length and ½ inches in width.

*Bract color*.—Light yellowish green (about RHS 141D); border 1/16 inches wide, purplish-red (about RHS 188D).

*Bract length*.—⅞ to 1¼ inches.

*Flower scape length*.—26 to 28 inches tall.

*Flower scape color*.—Purplish-red (about RHS 178C).

*Flower scape angle*.—Arching 25 to 30 degrees from vertical.

*Pedicel color*.—Moderate purplish red (about RHS 184D).

*Pedicel dimensions*.—⅝ inches in length and ⅛ inches in width.

*Raceme length*.—12 to 16 inches from lowest flower to top of inflorescence.

Scape description:

*Number*.—The number of scapes per plant is dependent on the maturity of the plant. Each mature eye comprising the clump may produce a single flower scape under normal growing conditions.

Description of reproductive organs: The reproductive organs are typical of the genus *Hosta* and comprise six stamens and a compound ovary having three locules. The stamen color is yellowish white (about RHS 155B); the anther color is moderate red (about RHS 183C); the pistil color is yellowish white (about RHS 155B); and the stigma color is yellowish white (about RHS 155B). The stamen length is about 2½ inches and the pistil length is about 2¾ inches, curved 180 degrees at the end.

Fruit: Tri-dehiscent capsule about 1⅛ inches long and 3/16 inches in diameter; variable in color strong yellowish green (about RHS143C) with more red or more green.

Seed development: Single winged drupe about ½ inches long and ⅛ inches wide, number per pod variable about 5 to 10, color dark gray purple (about RHS 202A).

Root development: From transfer to rooting media in tissue culture, rooting takes approximately 4 weeks at about 68 degrees Fahrenheit. After transfer from stage III in tissue culture to planting into soil in a greenhouse, a well rooted plant is produced in approximately 8 weeks with a day-time temperature of about 68 degrees Fahrenheit and a soil temperature of about 78 degrees Fahrenheit.

I claim:

1. A new and distinct cultivar of *Hosta* plant named 'First Blush' as illustrated and described herein.

* * * * *